United States Patent
Sappey et al.

(10) Patent No.: US 9,163,987 B2
(45) Date of Patent: Oct. 20, 2015

(54) DEFECT INSPECTION AND PHOTOLUMINESCENCE MEASUREMENT SYSTEM

(75) Inventors: Roman Sappey, San Jose, CA (US); Steven W. Meeks, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 803 days.

(21) Appl. No.: 12/861,894

(22) Filed: Aug. 24, 2010

(65) Prior Publication Data

US 2012/0049085 A1 Mar. 1, 2012

(51) Int. Cl.

| | |
|---|---|
| F21V 9/16 | (2006.01) |
| G01J 3/36 | (2006.01) |
| G01J 3/44 | (2006.01) |
| G01N 21/64 | (2006.01) |
| G01N 21/95 | (2006.01) |

(52) U.S. Cl.
CPC .............. G01J 3/36 (2013.01); G01J 3/4412 (2013.01); G01N 21/6489 (2013.01); G01N 21/9501 (2013.01)

(58) Field of Classification Search
USPC .............. 250/458.1, 459.1; 356/72, 300, 445, 356/237.1
See application file for complete search history.

(56) References Cited

U.S. PATENT DOCUMENTS

| | | | |
|---|---|---|---|
| 4,626,101 A * | 12/1986 | Ogawa et al. ............... | 356/237.2 |
| 6,069,690 A * | 5/2000 | Xu et al. ........................ | 356/73 |
| 6,791,099 B2 | 9/2004 | Some et al. | |
| 7,274,445 B1 | 9/2007 | Meeks | |
| 8,823,935 B1 | 9/2014 | Meeks et al. | |
| 2002/0109110 A1* | 8/2002 | Some et al. ................. | 250/559.4 |
| 2009/0250628 A1* | 10/2009 | Mano ........................... | 250/458.1 |
| 2010/0020312 A1 | 1/2010 | Jeong et al. | |

FOREIGN PATENT DOCUMENTS

| | | |
|---|---|---|
| CN | 1496478 A | 5/2004 |
| JP | S61-228332 A | 10/1986 |
| JP | 11211668 A | 8/1999 |
| JP | 2000-346802 A | 12/2000 |
| JP | 2003-098089 A | 4/2003 |
| JP | 2008-128811 A | 6/2008 |
| JP | 2008164399 A | 7/2008 |

* cited by examiner

*Primary Examiner* — Rafferty Kelly
(74) *Attorney, Agent, or Firm* — Suiter Swantz pc llo (57) ABSTRACT

A system for defect detection and photoluminescence measurement of a sample may include a radiation source configured to target radiation to the sample. The system may also include an optics assembly positioned above the sample to receive a sample radiation. The system may also include a filter module configured to receive the sample radiation collected by the optics assembly. The filter module may separate the sample radiation collected by the optics assembly into a first radiation portion and a second radiation portion. The system may also include a defect detection module configured to receive the first radiation portion from the filter module. The system may further include a photoluminescence measurement module configured to receive the second radiation portion from the filter module. The defect detection module and the photoluminescence measurement module may be configured to receive the respective first radiation portion and the second radiation portion substantially simultaneously.

21 Claims, 6 Drawing Sheets

```
┌─────────────────────────────────────────────────────────────┐
│ 210   irradiating the sample                                │
└─────────────────────────────────────────────────────────────┘
                              │
                              ▼
┌─────────────────────────────────────────────────────────────┐
│ 220   collecting radiation from the sample, the collected   │
│ radiation including radiation which is at least one of      │
│ reflected by, scattered by, or radiated from the sample     │
└─────────────────────────────────────────────────────────────┘
                              │
                              ▼
┌─────────────────────────────────────────────────────────────┐
│ 230   filtering the collected radiation between a first     │
│ radiation portion and a second radiation portion            │
└─────────────────────────────────────────────────────────────┘
                              │
                              ▼
┌─────────────────────────────────────────────────────────────┐
│ 240   passing the first radiation portion to a defect       │
│ detection module                                            │
└─────────────────────────────────────────────────────────────┘
                              │
                              ▼
┌─────────────────────────────────────────────────────────────┐
│ 250   passing the second radiation portion to a             │
│ photoluminescence measurement module                        │
└─────────────────────────────────────────────────────────────┘
                              │
                              ▼
┌─────────────────────────────────────────────────────────────┐
│ 260   analyzing the first radiation portion and the second  │
│ radiation portion substantially simultaneously              │
└─────────────────────────────────────────────────────────────┘
```

DEFECT INSPECTION AND PHOTOLUMINESCENCE MEASUREMENT SYSTEM

FIELD

The present disclosure generally relates to the field of inspection systems, and more particularly to a defect inspection and photoluminescence measurement system.

BACKGROUND

Adequately monitoring performance of deposition processes used during electronics production (e.g., high-brightness LED production) is important to ensuring the quality of and consistency of a relatively time-intensive procedure. Various ex-situ processes may be utilized, including photoluminescence (PL) mapping and defect inspection. Under specific excitation conditions, the local photoluminescence spectrum may be indicative of what the emission spectrum will be of an LED from the measured region of a wafer once made into a device. Measured non-uniformity of a PL peak wavelength may be traced to various process conditions, including temperature variations or gradients, which may be utilized to correct undesired process conditions.

Defect inspection may be utilized to detect and monitor various defects in the wafer, including sizes/types of surface imperfections, particles, irregularities in the thickness of epi-layers, and the like, which may hamper the performance of the semiconductor material. Defect inspection may be utilized subsequent to deposition techniques, and therefore the results of a defect inspection may be utilized to detect a defect relatively early in a manufacturing process prior to assembly of a finished product.

Currently, in order to perform both PL mapping and defect detection, two separate platforms are utilized. Such a configuration presents undesired consequences including the costs associated with owning/maintaining two separate platforms, multiple steps of handling a wafer (which increases the risk of contamination to the wafers), difficulty in correlating the separate data from the separate platforms, and the time and costs associated with performing two separate monitoring techniques.

It is therefore desirable to provide a defect inspection and photoluminescence measurement system which addresses the above-mentioned limitations of using two separate platforms, sequentially or otherwise. In addition, it is desirable to provide a defect inspection and photoluminescence measurement system such that the combination of scatter data and PL data taken at the same high resolution may enable a new level of characterization and understanding of certain defect types (e.g. those relevant to the fabrication of high-brightness LEDs).

SUMMARY

A system for defect detection and photoluminescence measurement of a sample may include, but is not limited to, a radiation source configured to target radiation to the sample. The system may also include an optics assembly positioned above the sample to receive a sample radiation. The sample radiation may be radiation which is at least one of reflected by, scattered by, or radiated from the sample, the optics assembly configured to reflect and/or refract the sample radiation. The system may also include a filter module configured to receive the sample radiation reflected or refracted by the optics assembly. The filter module may separate the sample radiation reflected and/or refracted by the optics assembly into a first radiation portion and a second radiation portion. The system may also include a defect detection module configured to receive the first radiation portion from the filter module. The system may further include a photoluminescence measurement module configured to receive the second radiation portion from the filter module. The defect detection module and the photoluminescence measurement module may be configured to receive the respective first radiation portion and the second radiation portion substantially simultaneously.

A method for detecting defects and measuring photoluminescence of a sample may include, but is not limited to, irradiating the sample, collecting radiation from the sample, the collected radiation including radiation which is at least one of reflected by, scattered by, or radiated from the sample, filtering the collected radiation between a first radiation portion and a second radiation portion, passing the first radiation portion to a defect detection module, passing the second radiation portion to a photoluminescence measurement module, and analyzing the first radiation portion and the second radiation portion substantially simultaneously.

A method for detecting defects and measuring photoluminescence of a sample may include, but is not limited to, irradiating the sample, collecting radiation from the sample, the collected radiation including radiation which is at least one of reflected by, scattered by, or radiated from the sample, filtering the collected radiation between a first radiation portion and a second radiation portion, passing the first radiation portion to a defect detection module, passing the second radiation portion to a photoluminescence measurement module, detecting a scattered defect in at least one of the first radiation portion or the second radiation portion, identifying a site of interest on the sample according to the scattered defect and measuring a spectral photoluminescence of the site of interest.

It is to be understood that both the foregoing general description and the following detailed description are exemplary and explanatory only and are not necessarily restrictive of the disclosure as claimed. The accompanying drawings, which are incorporated in and constitute a part of the specification, illustrate an embodiment of the disclosure and together with the general description, serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the presently preferred embodiments of the present invention, examples of which are illustrated in the accompanying drawings.

Figure 1:
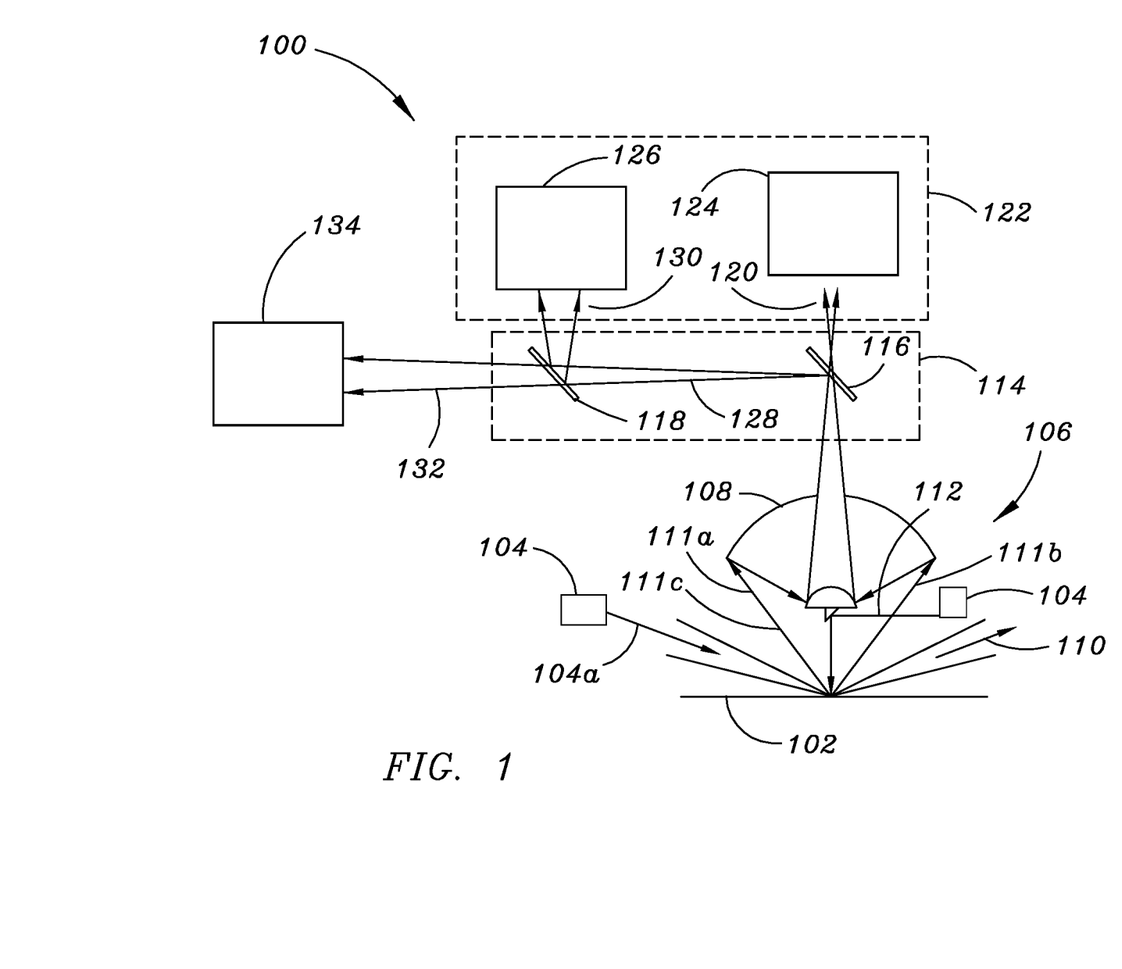
FIG. 1 is a schematic illustration of one embodiment of a system for simultaneous defect inspection and photoluminescence (PL) measurement.

Referring now to FIG. 1, a schematic illustration of one embodiment of a system 100 for defect inspection and photoluminescence (PL) measurement of a wafer sample 102 is shown. The system 100 may include a radiation source 104 configured to target radiation to the wafer 102. In the embodiment shown in FIG. 1, the radiation source 104 may generate an oblique input laser beam 104a, which may be directed at the sample of interest 102 (e.g. an epi wafer after MOCVD deposition) under a light collector 108 of the optics assembly 106. The optics assembly 106 may be a reflective or refractive objective configured to receive wafer radiation, where the wafer radiation may include radiation which is at least one of reflected by, scattered by, or radiated from the wafer 102. For example, a portion 110 of the input laser beam 104a may reflect from the top surface of the wafer 102, a portion 111a of the input laser beam 104a may be scattered from the top surface of the wafer 102 into the light collector 108 (another scattered portion 111b is described below), and a portion 111c may be absorbed and reemitted/radiated (photoluminescence (PL)) by the active structure (e.g. a multi-quantum well (MQW)) or any other fluorescence properties of the sample 102 under test. The reflected portion 110 of the radiation may be used to provide information on the reflectivity, slopes, or defects of the sample surface 102. The scattered and reemitted/radiated portions (111a, 111b, and 111c) may be collected by the optics assembly 106 of system 100 to provide defect detection, classification, and photoluminescence measurement data.

As shown in FIG. 1, the radiation source 104 may be configured to target an incident laser beam 112, which may be sent at substantially normal incidence to the sample 102. For instance, the incident laser beam 112 may utilize the optical assembly 106 to direct the incident laser beam 112 substantially normal to the wafer 102. The incident laser beam 112 may also reflect, scatter, and radiate from the sample 102. The scattered portion 111b of the incident laser beam 112 is shown in FIG. 1. In one embodiment, the incident laser beam 112 has a wavelength longer than a wavelength of the oblique input laser beam 104a. For instance, in one particular embodiment, the radiation source 104 is configured to generate the oblique input laser beam 104a at approximately 405 nm and is configured to generate the normally incident laser beam 112 at approximately 660 nm. It may be appreciated that radiation of other wavelengths may be utilized without departing from the scope of the present disclosure. At least a portion of at least one of the scattered, reflected, or radiated portion of the incident laser beam 112 may enter the light collector 108 of the optics assembly 106. For example, the scattered portion 111b may be collected by the light collector 108 of the optics assembly 106. As shown in FIG. 1, the scattered portion 111b may be collected substantially simultaneously with the scattered portion 111a of the input laser beam 104a and with the PL portion 111c of the input laser beam 104a.

The light collector 108 of FIG. 1 may be of the finite conjugate type, and thus the collected light 111a, 111b, and 111c (scattered portions of the oblique input laser beam 104a and the normally incident laser beam 112, as well as photoluminescence from the sample 102) may be diverged to a set of optics and detectors that perform the photoluminescence measurement and the scattered light detection at a plurality of laser wavelengths. A finite conjugate type collector may be used so that a pinhole (or field stop) may be placed at the back focal position of the collector. In this case the pinhole would be placed in beam path 120 just beyond filter 116 and in beam path 128 just to the left of filter 116. The pinhole or slit serves as a spatial filter to remove scattered light whose origin is not from light which is scattered by the surface 102. For instance, stray light from the laser source 104 or light scattered from the inside or the backside of sample 102. The optics assembly 106 may further be configured to reflect or refract the wafer radiation to a set of optics and detectors, as described below.

The system 100 may include a filter module 114 configured to receive the wafer radiation (e.g., the collected light 111a, 111b, and 111c) reflected and/or refracted by the optics assembly 106. The filter module 114 may be configured to separate the wafer radiation into a first radiation portion and a second radiation portion. The filter module 114 may include a first filter 116 and a second filter 118. In one particular embodiment, the first filter 116 and the second filter 118 are dichroic beamsplitters configured to pass light of specified wavelengths while reflecting light other than the specified wavelengths. The wafer radiation collected by the light collector 108 and reflected and/or refracted may impinge on the first filter 116. The first filter 116 may pass a majority of the portion of light 120 corresponding to the scattered light from the incident laser beam 112 to a defect detection module 122. For instance, in a particular embodiment, the portion of light 120 may be approximately 660 nm. The defect detection module 122 may be configured to receive light scattered from the wafer sample 102 to detect and monitor various defects in the wafer, including sizes/types of surface imperfections, particles, irregularities in the thickness of epi-layers, and the like, which may hamper the performance of the semiconductor material. In the embodiment shown in FIG. 1, the defect detection module 122 includes a first light detector 124 and a second light detector 126. In a particular embodiment, the first light detector 124 and the second light detector 126 are scattered light detectors, such as photomultiplier tubes. The first filter 116 may reflect a majority of the portion of light 128 corresponding to both the scattered light from the oblique input laser beam 104a and the photoluminescence from the wafer subsequent to application of the oblique input laser beam 104a. For instance, in a particular embodiment, the portion of light 128 may have a wavelength of less than approximately 650 nm.

The portion of light 128 may impinge on second filter 118, as shown in FIG. 1. The second filter 118 may reflect a majority of the portion of light 130 corresponding to the scattered light from the oblique input laser beam 104a, which may be sent to second light detector 126. For instance, in a particular embodiment, the portion of light 130 may be approximately less than 410 nm. The second filter 118 may pass the portion of light 132 originating from photoluminescence by the wafer sample 102. For instance, in a particular embodiment, the portion of light 132 may be between approximately 650 nm and 415 nm. Thus, where the filter module 114 includes the first filter 116 and the second filter 118, the filter module may be configured to separate the wafer radiation (e.g., 111a, 111b, and 111c) into a first radiation portion comprised of light portions 120 and 130 and a second radiation portion comprised of light portion 132. The first radiation portion (e.g., light portions 120 and 130) may be received by the defect detection portion 122, as described above, and the second radiation portion (e.g., light portion 132) may be received by a photoluminescence module 134, as described below. It may be appreciated that the first radiation portion and the second radiation portion may comprise differing portions of light depending on the type and amount of filters utilized in the filter module 114. For example, the first radiation portion and the second radiation portion may each include a single light portion or may include multiple light portions.

Figures 2, 3:
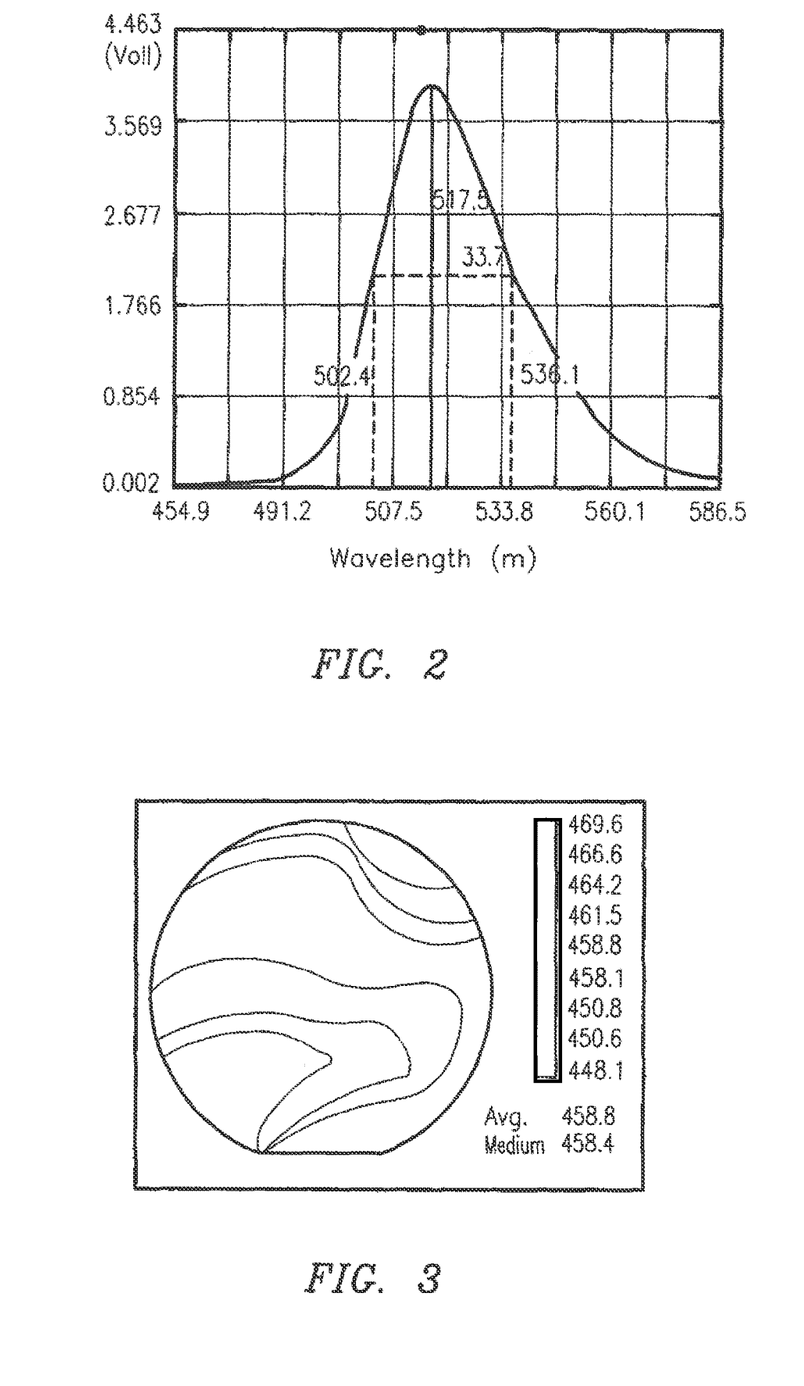
FIG. 2 is a graph of an example of a PL spectrum at one location of a wafer.
FIG. 3 is an illustration of a chart of a PL map for a peak wavelength of a wafer.

The portion of light 132 may pass to the photoluminescence measurement module 134 of the system 100. The photoluminescence measurement module 134 may detect and monitor a local photoluminescence spectrum from the sample 102, which may be indicative of what the emission spectrum will be of an LED from the measured region of the wafer 102 once made into a device, such as shown in FIG. 2, which provides a PL spectrum at one location of a green LED wafer.

The photoluminescence measurement module 134 may include a third light detector such as a photomultiplier, an avalanche photo-diode (APD), or another type of photo-diode, depending on the light level from the photo-luminescence and the required sensitivity. In a particular embodiment, the photoluminescence measurement module 134 includes a spectrometer, that may be fiber-coupled or not, configured to provide photoluminescence mapping at a rate sufficient to provide a color map of the photoluminescence (e.g., full spectral measurement of the photoluminescence), such as the example shown in FIG. 3, which provides a PL map for a peak wavelength from a blue LED wafer. A fiber-coupled ultra-fast spectrometer may enable a single pass measurement of the wafer sample 102 at a defect detection throughput of between approximately 15 to 25 wafers per hour for approximately four-inch wafers. This sampling rate may be slower than the sampling rate performed by the defect detection module 122. By utilizing photoluminescence mapping at this rate, wavelength variations and intensity variations may be obtained for the wafer sample 102, including resolution of the chromatic content of the portion of light 132.

Figure 4A:
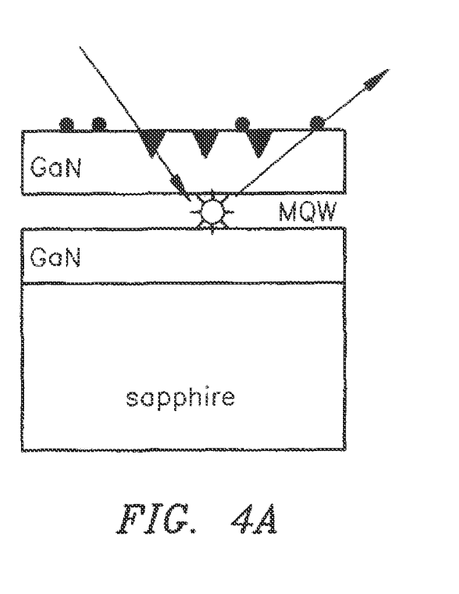
FIG. 4A is a schematic illustration of a PL procedure implemented on a wafer with a Gallium Nitride epi-layer and a sapphire substrate.
Figure 4B:
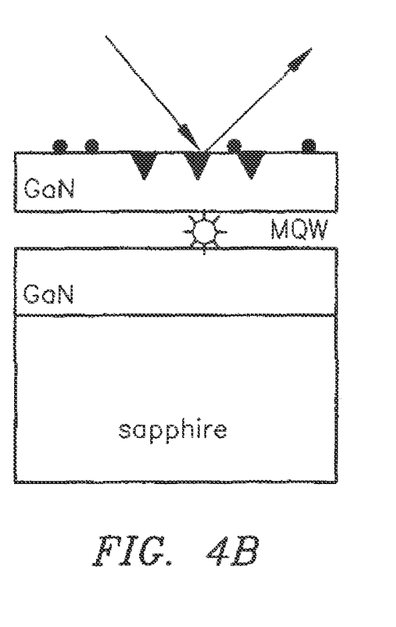
FIG. 4B is a schematic illustration of a defect detection procedure implemented on the wafer shown in FIG. 4A.
Figure 4C:
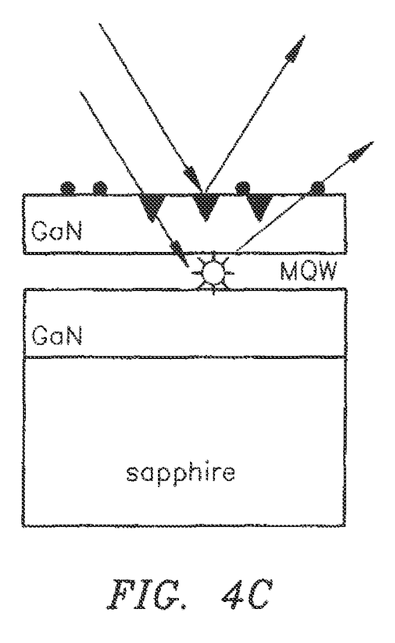
FIG. 4C is a schematic illustration of a simultaneous PL procedure and defect detection procedure implemented on the wafer shown in FIG. 4A.

As described above, the photoluminescence measurement module 134 may include a simple non-spectrometric light detector, such as a relatively fast photodiode to permit relatively high speed sampling. In this embodiment, an integrated photoluminescence may be obtained, which may correlate to a local internal quantum efficiency of a multiple quantum well (MQW) of the wafer sample 102. Thus, with the relatively high speed sampling, a high resolution luminosity map of the wafer sample 102 may be measured. The sampling rate may be similar to the sampling rate performed by the defect detection module 122, thereby allowing the photoluminescence measurement module 134 to sample as fast as the defect detection module 122. By co-sampling with the defect detection module 122 and the photoluminescence measurement module 134, the system 100 may permit viewing photoluminescence measurements simultaneously with defect detection measurements and at a substantially similar resolution. The data obtained by both modules may be used to correlate data directly between the observed data. For instance, scattered data may be obtained by the defect detection module 122 and the correlating data from the photoluminescence measurement module 134 (obtained substantially simultaneously with the scattered data) may be utilized to indicate that a pit in the wafer sample 102 disrupted the output of an MQW of the wafer sample 102. For instance, as shown in FIGS. 4A and 4B, photoluminescence and defect detection (respectively) may be separately measured to correlate respective abnormalities to adjust variables of the production process of the wafer (e.g., gas flow, temperature, and the like), but such separate measurements may be inefficient and may not correlate the photoluminescence measurements with the defect detection measurements. System 100 may operate to measure substantially simultaneously photoluminescence and defect detection, such as shown in FIG. 4C, which may correlate the photoluminescence measurements with the defect detection measurements for more focused adjustment of the production process of the wafer.

Figure 5:
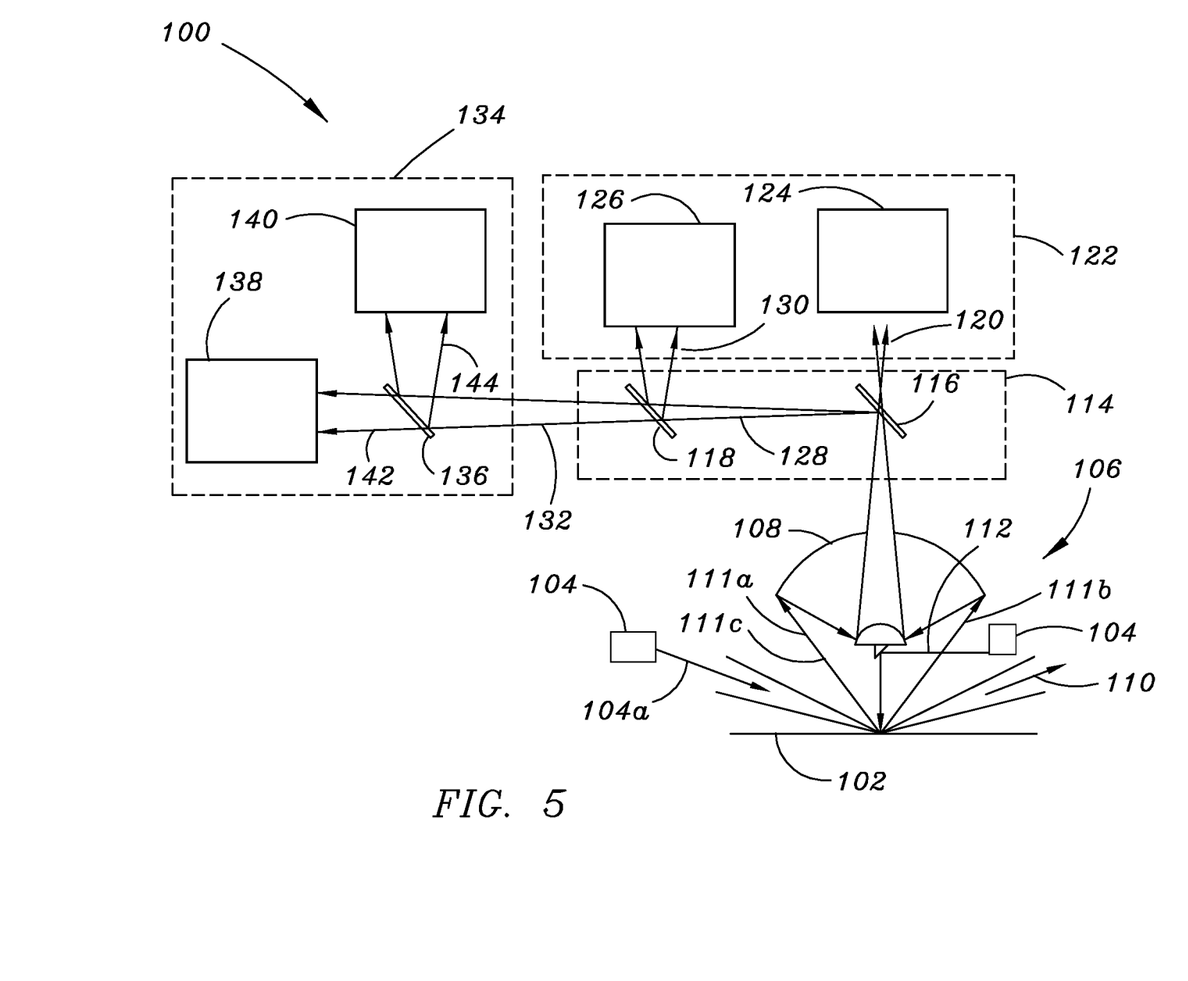
FIG. 5 is a schematic illustration of another embodiment of a system for simultaneous defect inspection and photoluminescence (PL) measurement.

Referring now to FIG. 5, a schematic illustration of another embodiment of the system 100 for simultaneous defect inspection and photoluminescence (PL) measurement is shown. In this embodiment, system may be configured substantially similarly to the embodiment shown in FIG. 1, however the photoluminescence measurement module 134 may include a beamsplitter 136, a first photo-detector 138, and a second photo-detector 140. As shown in FIG. 5, the portion of light 132 is split by the beamsplitter 136 into a first portion of light 142 and a second portion of light 144. The beamsplitter 136 may be a standard beamsplitter (e.g., broadband dielectric) so as to split the light (e.g., symmetrically or asymmetrically), rather than filter the light according to wavelength. The first portion of light 142 may be directed to the first photo-detector 138, which may be a photo-multiplier type of photo-detector configured for fast sampling rates and for obtaining an integrated photoluminescence measurement. The second portion of light 144 may be directed to the second photo-detector 140, which may be a spectrometer type of photo-detector configured for slower sampling rates and for obtaining full spectral measurements of the photoluminescence. In a particular embodiment, the second photo-detector 140 includes a fiber-coupler which interfaces with the second portion of light 144.

Alternatively, the beamsplitter 136 may be a fiber-coupler which includes a bifurcation to separate the portion of light 132 to each of the first photo-detector 138 and the second photo-detector 140.

Accordingly, the system 100 of FIG. 5 may enable substantially simultaneous defect detection, integrated photoluminescence measurement, and full spectral photoluminescence measurement on a single platform, with a single optical head. Additionally, the system 100 may enable the direct correlation of photoluminescence measurement (e.g., integrated and spectral measurements) with defect detection measurement. Such a configuration avoids the undesired consequences of two separate measurement platforms, including the costs associated with owning/maintaining two separate platforms, multiple steps of handling a wafer (which increases the risk of contamination to the wafers), difficulty in correlating the separate data from the separate platforms, and the time and costs associated with performing two separate monitoring techniques.

Figure 6:
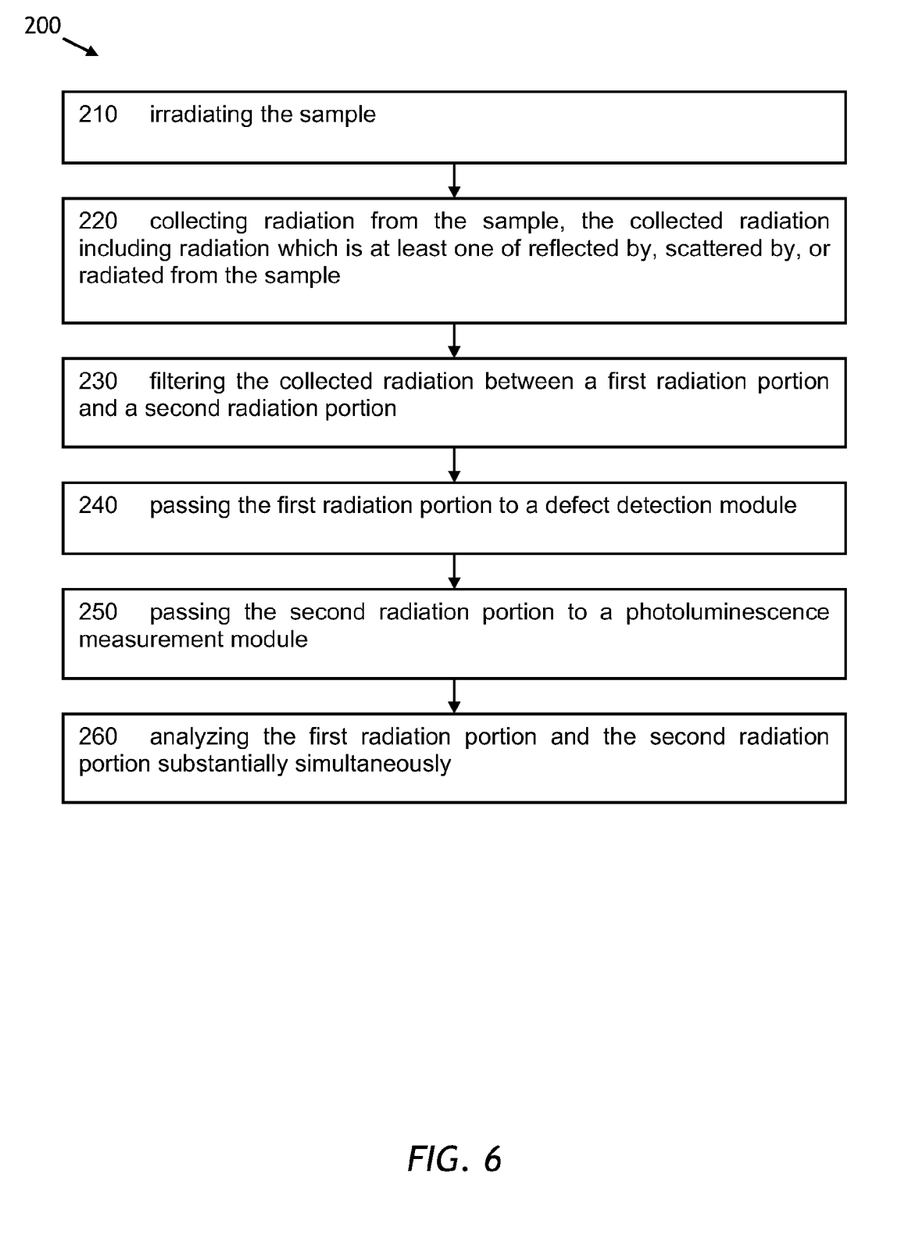
FIG. 6 is a flow chart of a method for detecting defects and measuring photoluminescence of a sample.

Referring now to FIG. 6, a flow chart of a method 200 for detecting defects and measuring photoluminescence of a sample is shown. The method 200 may include irradiating the sample 210. For instance, the sample may be irradiated with oblique input laser beam 104a and/or normally incident laser beam 112 from radiation source 104. The method 200 may include collecting radiation from the sample, the collected radiation including radiation which is at least one of reflected by, scattered by, or radiated from the wafer 220. The radiation from the sample may be collected by the optics assembly 106. The method 200 may include filtering the collected radiation between a first radiation portion and a second radiation portion 230. The collected radiation may be filtered by the filter module 114. The method 200 may include passing the first radiation portion to a defect detection module 240. For instance, the first radiation portion may be at least one of the portion of light 120 or the portion of light 130 passed to the defect detection module 122. In one particular embodiment, the first radiation portion includes both scattered light portions 120 and 130 filtered by the filter module 114. The method 200 may include passing the second radiation portion to a photoluminescence measurement module 250. For instance, the second radiation portion may include the portion of light 132 passed to the photoluminescence measurement module 134 from the filter module 114. The method 200 may include analyzing the first radiation portion and the second radiation portion substantially simultaneously 260. For instance, since the system 100 may utilize a single optical head for the defect detection module 122 and the photoluminescence measurement module 134, the first radiation portion and the second radiation portion may be analyzed substantially simultaneously, enabling correlation of the PL measurements and the defect detection.

Figure 7:
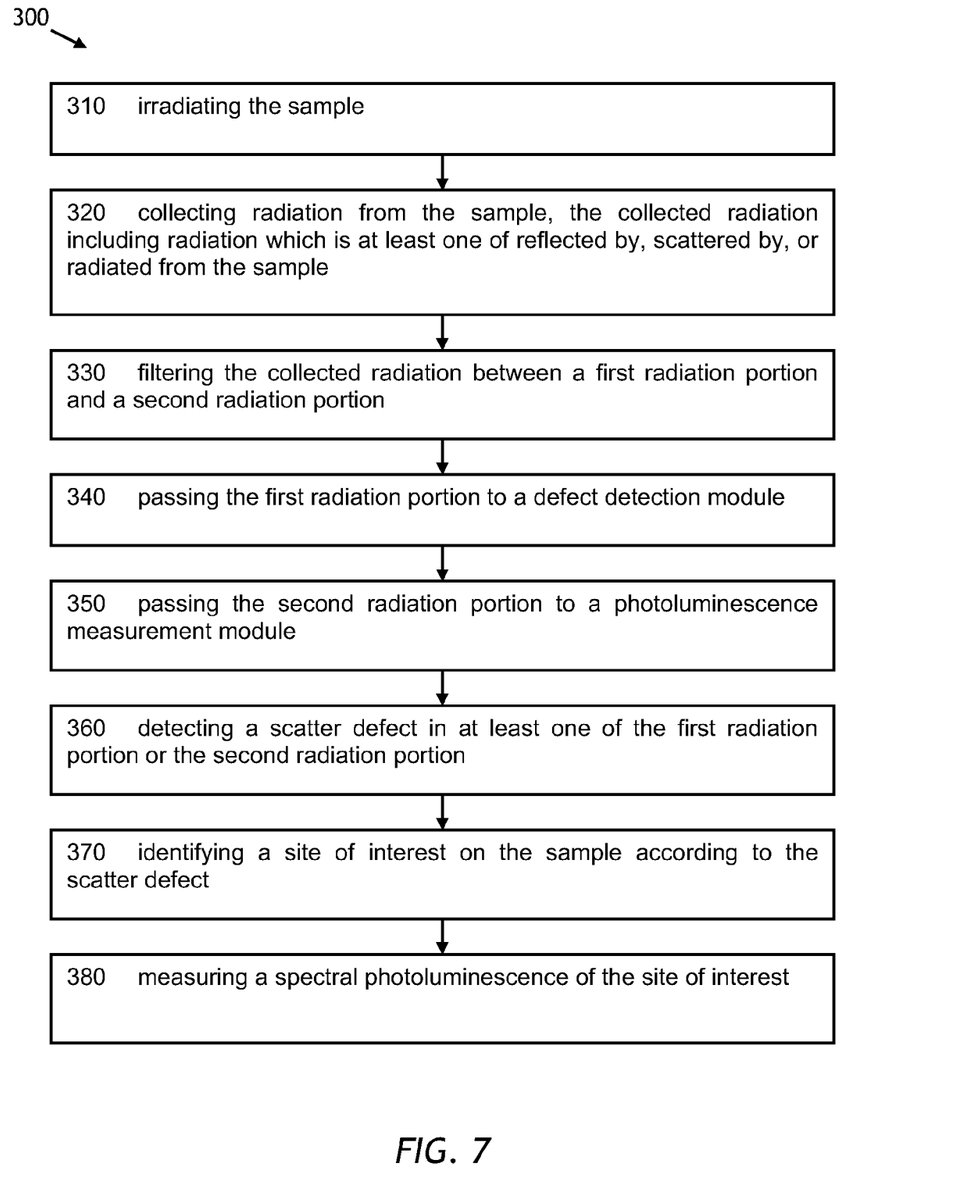
FIG. 7 is a flow chart of another method for detecting defects and measuring photoluminescence of a sample.

Referring now to FIG. 7, a flow chart of a method 300 for detecting defects and measuring photoluminescence of a sample is shown. The method 300 may include irradiating the sample 310. For instance, the sample may be irradiated with oblique input laser beam 104a and/or normally incident laser beam 112 from radiation source 104. The method 300 may include collecting radiation from the sample, the collected radiation including radiation which is at least one of reflected by, scattered by, or radiated from the wafer 320. The radiation from the sample may be collected by the optics assembly 106. The method 300 may include filtering the collected radiation between a first radiation portion and a second radiation portion 330. The collected radiation may be filtered by the filter module 114. The method 300 may include passing the first radiation portion to a defect detection module 340. For instance, the first radiation portion may be at least one of the portion of light 120 or the portion of light 130 passed to the defect detection module 122. In one particular embodiment, the first radiation portion includes both scattered light portions 120 and 130 filtered by the filter module 114. The method 300 may include passing the second radiation portion to a photoluminescence measurement module 350. For instance, the second radiation portion may include the portion of light 132 passed to the photoluminescence measurement module 134 from the filter module 114. The method 300 may include detecting a scatter defect in at least one of the first radiation portion or the second radiation portion 360. The scatter defect may be detected by at least one of the defect detection module 122 or the photoluminescence measurement module 134 (e.g., when the photoluminescence measurement module 134 includes a photo-multiplier type of photo-detector configured for fast sampling rates and for obtaining an integrated photoluminescence measurement). The method 300 may include identifying a site of interest on the sample according to the scatter defect 370. For instance, defects in the sample may be identified by performing a relatively fast scan rate of a sample, and location data of the defect on the sample may be saved in a computer memory. The method 300 may include measuring a spectral photoluminescence of the site of interest 380. For instance, the photoluminescence measurement module 134 may include a spectrometer to measure spectral photoluminescence of the sample at the site of interest with a relatively slower scan rate. However, since the site of interest is determined according to a relatively fast scan rate procedure, only the sites of interest (as opposed to the entire sample) may be subjected to the relatively slower scan rate of a spectrometer-based PL measurement, thereby increasingly the overall efficiency of the wafer analysis.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components thereof without departing from the scope and spirit of the disclosure or without sacrificing all of its material advantages. The form herein before described being merely an explanatory embodiment thereof, it is the intention of the following claims to encompass and include such changes.

What is claimed is:

1. A system for defect detection and photoluminescence measurement of a sample, comprising:
   a radiation source configured to target radiation to the sample;
   an optics assembly positioned above the sample to receive a sample radiation, the sample radiation being radiation which is at least one of reflected by, scattered by, or radiated from the sample, the optics assembly configured to collect the sample radiation;
   a filter module configured to receive the sample radiation collected by the optics assembly, the filter module separating the sample radiation collected by the optics assembly into a first radiation portion and a second radiation portion;
   a defect detection module configured to receive the first radiation portion from the filter module, the defect detection module configured to detect at least one defect of the sample utilizing the first radiation portion; and
   a photoluminescence measurement module configured to receive the second radiation portion from the filter module, the photoluminescence measurement module including a spectrometer configured to detect a local photoluminescence spectrum of the sample utilizing the second radiation portion, the photoluminescence measurement module configured to provide a photoluminescence mapping based upon the detected local photoluminescence spectrum, the defect detection module and the photoluminescence measurement module configured to receive the respective first radiation portion and the second radiation portion substantially simultaneously.

2. The system of claim 1, further comprising:
   a fiber coupler between the spectrometer and the second radiation portion.

3. The system of claim 1, further comprising:
   a photo-detector; and
   a bifurcated fiber coupler, the bifurcated coupler located between the second radiation portion and each of the photo-detector and the spectrometer, the bifurcated fiber coupler passing at least a portion of the second radiation portion to each of the photo-detector and the spectrometer.

4. The system of claim 1, wherein the filter module includes a first filter and a second filter.

5. The system of claim 4, wherein the first filter is configured to substantially separate the sample radiation into a first filtered portion from a second filtered portion, and the second filter is configured to receive the second filtered portion from the first filter.

6. The system of claim 5, wherein the second filter is configured to substantially separate a third filtered portion from a fourth filtered portion.

7. The system of claim 6, wherein the defect detection module includes a first light detector and a second light detector, the first light detector is configured to receive the first filtered portion, and the second light detector is configured to receive the third filtered portion.

8. The system of claim 6, wherein the first filtered portion has a first wavelength, the second filtered portion is less than a second wavelength, the third filtered portion is greater than a third wavelength, and the fourth filtered portion is less than a fourth wavelength.

9. The system of claim 8, wherein the first wavelength is approximately 660 nanometers, the second wavelength is approximately 650 nanometers, the third wavelength is approximately 415 nanometers, and the fourth wavelength is approximately 410 nanometers.

10. The system of claim 4, wherein the defect detection module includes a first radiation detector and a second radiation detector, the first radiation detector is configured to receive radiation from the first filter, and the second radiation detector is configured to receive radiation from the second filter.

11. The system of claim 1, wherein the radiation source includes a first radiation source and a second radiation source.

12. The system of claim 11, wherein the first radiation source is configured to generate an oblique input laser beam directed at the sample, and the second radiation source is configured to generate a substantially normal incident laser beam.

13. The system of claim 12, wherein the first radiation portion includes at least one of scattered radiation from the oblique input laser beam or scattered radiation from the substantially normal incident laser beam, and the second radiation portion includes photoluminescence from the sample.

14. The system of claim 1, wherein the defect detection module and the photoluminescence measurement module share an optical head.

15. The system of claim 1, wherein the photoluminescence measurement module is further configured to determine an emission spectrum of a light emitting diode fabricated from at least a portion of the sample based upon the photoluminescence mapping.

16. The system of claim 1, wherein at least one of the defect detection module and the photoluminescence measurement module is configured to correlate detected defect information and the photoluminescence mapping, and further configured to determine an adjustment for at least one semiconductor production variable based upon said correlation.

17. A method for detecting defects and measuring photoluminescence of a sample, comprising:
    irradiating the sample;
    collecting radiation from the sample, the collected radiation including radiation which is at least one of reflected by, scattered by, or radiated from the sample;
    filtering the collected radiation between a first radiation portion and a second radiation portion;
    passing the first radiation portion to a defect detection module;
    passing the second radiation portion to a photoluminescence measurement module;
    analyzing the first radiation portion and the second radiation portion substantially simultaneously, including:
        detecting at least one defect of the sample, via the defect detection module, utilizing the first radiation portion,
        detecting a local photoluminescence spectrum of the sample, via the photoluminescence measurement module, utilizing the second radiation portion, and providing a photoluminescence mapping based upon the detected local photoluminescence spectrum;
    correlating detected defect information and the photoluminescence mapping; and
    adjusting at least one semiconductor production variable based upon said correlation.

18. The method of claim 17, wherein detecting the local photoluminescence spectrum from the sample includes:
    measuring a spectral photoluminescence from the second radiation portion.

19. The method of claim 17, wherein detecting the local photoluminescence spectrum from the sample includes:
    measuring a spectral photoluminescence from the second radiation portion; and
    measuring an integrated photoluminescence from the second radiation portion.

20. The method of claim 17, wherein detecting the local photoluminescence spectrum from the sample includes:
    measuring an integrated photoluminescence from the second radiation portion.

21. A method for detecting defects and measuring photoluminescence of a sample, comprising:
    irradiating the sample;
    collecting radiation from the sample, the collected radiation including radiation which is at least one of reflected by, scattered by, or radiated from the sample;
    filtering the collected radiation between a first radiation portion and a second radiation portion;
    passing the first radiation portion to a defect detection module;
    passing the second radiation portion to a photoluminescence measurement module substantially simultaneous to passing the first radiation portion to the defect detection module;
    detecting a scattered defect of the sample, via the defect detection module, utilizing the first radiation portion;
    identifying a site of interest on the sample according to the scattered defect;
    detecting a local photoluminescence spectrum of the sample by at least measuring a spectral photoluminescence of the site of interest, via the photoluminescence measurement module, utilizing the second radiation portion;
    providing a photoluminescence mapping based upon the spectral photoluminescence of the site of interest; and
    determining an emission spectrum of a light emitting diode fabricated from at least a portion of the sample including the sight of interest based upon the photoluminescence mapping.

* * * * *